United States Patent [19]

Hsu et al.

[11] Patent Number: 5,541,167
[45] Date of Patent: Jul. 30, 1996

[54] THROMBORESISTANT COATING FOR DEFOAMING APPLICATIONS

[75] Inventors: Li-Chien Hsu, Mission Viejo; Mark E. Loar, Irvine, both of Calif.

[73] Assignee: Baxter International Inc., Deerfield, Ill.

[21] Appl. No.: 331,292

[22] Filed: Oct. 28, 1994

Related U.S. Application Data

[63] Continuation of Ser. No. 179,886, Jan. 10, 1994, abandoned, which is a continuation of Ser. No. 46,503, Apr. 12, 1993, abandoned, which is a continuation of Ser. No. 708,603, May 31, 1991, abandoned.

[51] Int. Cl.$^6$ .......................... A61L 33/00; A61K 31/725
[52] U.S. Cl. .................. 514/56; 536/21; 536/55.3; 536/124; 523/112; 604/4; 604/317
[58] Field of Search .................. 514/56; 536/21, 536/124, 55.3; 523/112; 604/4, 317

[56] References Cited

U.S. PATENT DOCUMENTS

| | | | |
|---|---|---|---|
| 3,434,869 | 3/1969 | Davidson et al. | 604/266 |
| 3,475,358 | 10/1969 | Bixler et al. | 523/112 |
| 3,717,502 | 2/1973 | Masubara et al. | 623/1 |
| 3,755,218 | 8/1973 | Yen et al. | 428/35.5 |
| 3,846,353 | 11/1974 | Grotta | 523/112 |
| 3,853,804 | 12/1974 | Yen et al. | 524/233 |
| 4,082,727 | 4/1978 | Nagata et al. | 525/54.2 |
| 4,116,898 | 9/1978 | Dudley et al. | 424/78.27 |
| 4,349,467 | 9/1982 | Williams et al. | 525/54.2 |
| 4,367,749 | 1/1983 | Dudley et al. | 128/637 |
| 4,572,724 | 2/1986 | Rosenberg et al. | 96/6 |
| 4,604,412 | 8/1986 | Joh et al. | 523/112 |
| 4,654,327 | 3/1987 | Teng | 514/56 |
| 4,662,906 | 5/1987 | Matkovich et al. | 96/6 |
| 4,676,975 | 6/1987 | McGary et al. | 424/423 |
| 4,678,468 | 7/1987 | Hiroyoshi | 623/1 |
| 4,698,207 | 10/1987 | Bringham et al. | 422/46 |
| 4,713,402 | 12/1987 | Solomon | 523/112 |
| 4,871,357 | 10/1989 | Hsu et al. | 604/266 |
| 4,876,066 | 10/1989 | Bringham et al. | 422/46 |
| 4,895,566 | 1/1990 | Lee | 604/266 |
| 4,944,767 | 7/1990 | Barbucci et al. | 623/66 |
| 5,000,764 | 3/1991 | Oshiyama et al. | 96/219 |
| 5,013,717 | 5/1991 | Solomon et al. | 514/56 |
| 5,028,597 | 7/1991 | Kodama et al. | 514/56 |
| 5,047,020 | 9/1991 | Hsu | 604/266 |
| 5,049,403 | 9/1991 | Larm et al. | 427/2.1 |
| 5,061,738 | 10/1991 | Solomon et al. | 523/100 |

FOREIGN PATENT DOCUMENTS

| | | |
|---|---|---|
| 0124200 | 2/1984 | European Pat. Off. . |
| 0184465 | 6/1986 | European Pat. Off. . |
| 0273700 | 7/1988 | European Pat. Off. . |
| 0338418 | 4/1989 | European Pat. Off. . |
| 0350161 | 1/1990 | European Pat. Off. . |
| 1153824 | 1/1967 | United Kingdom . |
| 1136669 | 4/1967 | United Kingdom . |
| 1319007 | 11/1971 | United Kingdom . |

OTHER PUBLICATIONS

*The Merck Index*, 10th Ed. p. 682 #4613 (1983).
Kim; Chemical Abstracts 106:143910q (1987).
Grainger et al; Chemical Abstracts 108:156451g (1988).
Dow Corning Medical Products; Bulletin 51–20A (1977).

*Primary Examiner*—Douglas W. Robinson
*Assistant Examiner*—Kathleen Kahler Fonda
*Attorney, Agent, or Firm*—Raymond Sun

[57] ABSTRACT

A composition for coating medical blood contacting surfaces comprises a mixture of an anticoagulant and a defoaming agent. The coating composition is applied by either dipping the device into a solution containing the mixture or by spraying the mixture onto the surface. Alternatively, the surface can be sequentially dip coated and/or sprayed with the individual components. In a preferred embodiment, the anticoagulant is a quaternary ammonium complex of heparin, preferably stearyldimethylbenzyl ammonium heparin, and the antifoaming agent is a mixture of polydimethylsiloxane and silicon dioxide.

15 Claims, No Drawings

THROMBORESISTANT COATING FOR DEFOAMING APPLICATIONS

This is a continuation of U.S. patent application Ser. No. 08/179,886, filed Jan. 10, 1994, now abandoned, which is a continuation of U.S. patent application Ser. No. 08/046,503, filed Apr. 12, 1993, now abandoned, which is a continuation of U.S. patent application Ser. No. 07/708,603, filed May 31, 1991, now abandoned.

FIELD OF THE INVENTION

This invention relates to a biocompatible coating composition which is to be applied to blood processing devices such as oxygenators and cardiotomy reservoirs. More specifically, the invention relates to a coating composition that combines antithrombogenicity with antifoaming characteristics.

BACKGROUND OF THE INVENTION

Recent advances in medical technology have caused the proliferation of man made devices which are utilized for blood processing. During blood processing, air is often mixed with the blood necessitating the removal of air bubbles or the "defoaming" of the blood before returning it to the patient. During open heart surgery, for example, extracorporeal medical devices are utilized to oxygenate and/or regulate the temperature of blood in the extracorporeal circuit. Certain devices are utilized within the circuit to "defoam" or remove excessive air bubbles which may be present in the blood. Bubble oxygenators, for example, must have a very efficient defoaming section to remove gas bubbles from oxygenated blood. One such defoaming device is the cardiotomy reservoir, which, in addition to its blood storing capability, removes a large quantity of air and impurities generated during intracardiac and intrapericardial suctioning. Other devices which may require blood defoaming include blood filters, blood reservoirs, autotransfusion devices or any blood handling device wherein the blood may encounter air bubbles.

Defoaming is typically accomplished by providing a very large surface area which is covered by a defoaming agent. The surface area is usually composed of a synthetic material, such as polyurethane foam, polypropylene mesh, polyvinylchloride strips, or stainless steel wool. Various defoaming agents which prevent or dissipate foam are known to those skilled in the art. The most commonly used defoaming agents which are applied to blood contacting devices are polydimethylsiloxane or a mixture of polydimethylsiloxane and silicon dioxide. These compounds are presently manufactured by Dow Corning and marketed under the trademarks ANTIFOAM A® and SIMETHICONE®.

Despite the clinical success involved with the application of defoaming agents to such extracorporeal devices as bubble oxygenators and cardiotomy reservoirs, a serious and persistent problem is that significant blood trauma is caused by the blood-air interactions and the large synthetic blood contacting surfaces. Thus, in order to prevent thrombus formation, it has become essential to administer anticoagulant agents, such as coumadin or heparin. Since the direct administration of these agents to the patient may increase the risk of patient bleeding, attention has turned to treating medical articles themselves with anticoagulant agents.

What is needed, then, is a coating for medical devices that provides both defoaming characteristics as well as blood compatibility.

SUMMARY OF THE INVENTION

What is provided by the present invention is a biocompatible coating composition that, when applied to medical devices, provides defoaming properties as well as antithrombogenicity. The coating composition of the present invention removes excess air bubbles and reduces blood trauma during extracorporeal circulation. What is also provided by the present invention is a method of coating a medical article with the composite coating material.

In accordance with the present invention a coating material is provided which consists of a biologically active substance and a defoaming/antifoaming agent. The preferred biologically active substances are anticoagulants, such as heparin or hirudin. The defoaming agent can be any chemical substance possessing defoaming properties. The preferred defoaming agent is a mixture of polydimethylsiloxane and silicon dioxide, such as the compounds manufactured by Dow Corning and marketed under the trademarks ANTIFOAM A® and SIMETHICONE®.

In one embodiment, the anticoagulant and the antifoaming agent are dissolved in a solvent and the article which is to be treated is dipped in the solvent. Alternatively, solvent containing the anticoagulant and the antifoaming agent can be sprayed onto the medical article.

In another embodiment, the anticoagulant and the antifoaming agent are separately dissolved in their respective solvents and the medical article is sequentially dipped into each of the coating elements. In yet a further embodiment, either or both of the dip-coating steps can be replaced by spraying the coating component onto the medical article.

DETAILED DESCRIPTION OF THE INVENTION

As indicated above, the present invention relates to a method of coating medical articles and a coating composition that is both thromboresistant and capable of either eliminating foam or preventing the formation of foam in blood. The coating material consists of a biologically active substance and a defoaming agent. In a preferred embodiment the biologically active substance is an anticoagulant. Various anticoagulants and various antifoaming agents are well known to those skilled in the art. In a preferred embodiment, however, the anticoagulant is heparin and the defoaming agent is a mixture of polymethylsiloxane and silicon dioxide.

As is well known to those skilled in the art, anticoagulant agents, such as heparin and hirudin, may be applied to articles through either physical entrapment, covalent bonding or ionic bonding. A favored approach is to ionically bond heparin. More specifically, a complex of heparin with an amine is prepared, forming either a primary, secondary, tertiary or quaternary ammonium complex. The heparin complex is then bound, in the form of a coating, to the walls of medical articles. Examples of particular compositions of heparin coatings may be seen in U.S. Pat. No. 4,118,484, granted to Ericksson and U.S. Pat. No. 4,871,357, granted to Hsu, et al. A preferred approach is to use a quaternary ammonium complex. Among these are alkyldimethylbenzyl ammonium heparin, which includes stearyldimethylbenzyl ammonium heparin or benzylkonium heparin, and tridodecylmethyl ammonium heparin. The most preferred approach is to use stearyldimethylbenzyl ammonium heparin, commonly known as stearylkonium heparin.

Typical defoaming agents are comprised of both active compounds and carriers. Occasionally, the agents will also include a spreading agent. Typical active compounds include fatty acid amides, higher molecular weight polyglycols, fatty acid esters, fatty acid ester amides, polyalkyline glycols, organophosphates, metallic soaps of fatty acids, silicone oils, hydrophobic silica, organic polymers, saturated and unsaturated fatty acids, and higher alcohols. Typical carriers include paraffinic, napthenic, aromatic, chlorinated, or oxygenated organic solvents. Those skilled in the art will be able to determine the appropriate defoaming composition depending upon the application. The preferred defoaming agents to apply to blood contacting devices are polydimethylsiloxane or a mixture of polydimethylsiloxane and silicon dioxide. Thus, the preferred coating composition of the present invention is a mixture of stearyldimethylbenzyl ammonium heparin with polydimethylsiloxane and silicon dioxide.

The coating composition of the present invention can be applied to bubble oxygenators, blood filters, blood reservoirs, autotransfusion devices, cardiotomy reservoirs, or any medical devices with synthetic surfaces that directly contact blood.

The thromboresistant and defoaming properties can be achieved by dissolving the heparin complex and defoaming agent in a solvent and subsequently dip-coating the synthetic surface in the solution or spray coating the solution onto the device. Alternatively, the heparin complex and the defoaming agent can be separately dissolved in their respective solvents and the synthetic surface can then be sequentially coated, either with the heparin complex followed by the defoaming agent or vice verse. Alternatively, spray-coating can be utilized in place of dip-coating. As is evident herein and to those skilled in the art, any combination of dissolving the heparin complex and the defoaming agent and either spray or dip coating the device can be used to coat the device with the coating solution of the present invention.

Since the heparin complex contains a hydrophilic surfactant as a wetting agent, and the antifoaming agent is hydrophobic, it was expected that there would be some reduction in defoaming efficiency as a result of the addition of the heparin complex. It was felt that the advantage of making the surface antithrombogenic was worth a slight reduction in antifoaming efficiency. It has been found, unexpectedly, however, and it is an advantage of the composite coating of the present invention, that the treated surfaces exhibit defoaming properties which are at least comparable to like surfaces treated with the defoaming agent alone. In some instances it has been demonstrated that the composite coating exhibits defoaming properties that are superior to like surfaces which are treated just with the defoaming agent.

Furthermore, surfaces treated with the composite coating have the additional advantage of a high degree of blood compatibility. In-vitro and ex-vivo results indicate that surfaces treated with the composite coating exhibit significantly less deposition of blood components, i.e. red thrombi, after blood circulation, indicating reduced blood trauma.

The following examples and test results give greater illustration and understanding of the invention.

EXAMPLE 1

0.25 grams of heparin complex (stearyldimethylbenzyl ammonium heparin) and 38 grams of Antifoam A® (polydimethylsiloxane and silicon dioxide) were dissolved in a mixture of Freon TF and methylene chloride. Urethane defoamers were dipped in the solution and subsequently air dried. The defoamers were then assembled into a cardiotomy reservoir which was evaluated for defoaming efficiency, breakthrough volume, and for appearance after blood circulation.

Three bovine ex-vivo veno-venous bifurcation test studies were undertaken to evaluate the composite coating. In each of the three test regimens blood flow from a bovine was bifurcated to two cardiotomy reservoirs, one coated with the antifoaming agent and one coated with the composite coating. Performance data (See Table 1, below) from the three studies demonstrated an increase in defoaming ability for the "test units" (those coated with the composite coating). In all three studies, the "control units" (the cardiotomy reservoir treated with just antifoaming agent) stopped defoaming during the last thirty minutes. In test studies #1 and #3, the "test units" continued to defoam. In test study #2, even though the unit stopped defoaming after 103 minutes, it continued to defoam after the "control unit" failed. Thus, contrary to expectations, the composite coated units performed at least as well if not better than the units treated with just antifoaming agent. Furthermore, in addition to enhanced defoaming efficiency, the cardiotomy reservoir containing the composite coating showed reduced breakthrough volume and a significant reduction in thrombi formation compared to reservoirs which had been coated just with Antifoam A® (polydimethylsiloxane and silicon dioxide).

TABLE 1

Defoaming data for the "test" and "control" Cardiotomy reservoirs. All hold-up, wicking, and streaming height measurements were made relative to the constant 500 mL reservoir level. Activated clotting times were maintained at 4 × BL.

| Device | Elapsed Time (mins) | Test Period | Qg (LPM) | Qb (LPM) | Inlet Pressure (mmHg) | Hold-Up Height (in.) | Wicking Height (in.) | Streaming Height (in.) | Observations |
|---|---|---|---|---|---|---|---|---|---|
| Test | 5 | 1 | 0.5 | 0.5 | 0 | 0.25 | 0.25 | — | |
| Study #1 | 34 | 2 | 1 | 1 | 0 | NC | NC | — | |
| | 64 | 3 | 2 | 2 | 6–19 | NC | 1 | — | Wicking on the seam. |
| | 94 | 4 | 3 | 3 | 46 | 1 | 1 | — | Slight scud. |
| | 101 | 4 | 3 | 3 | 52 | NC | NC | — | Spotting on the seam. |
| Control | 5 | 1 | 0.5 | 0.5 | 0 | 0.25 | 1.25 | — | |
| Study #1 | 34 | 2 | 1 | 1 | 1–2 | NC | NC | — | Slight scud. |
| | 64 | 3 | 2 | 2 | 17–27 | 0.5 | 1.5 | — | Spotting. |
| | 94 | 4 | 3 | 3 | 72 | — | — | 6 | FAILURE |
| Test | 3 | 1 | 0.5 | 0.5 | 0 | 0.25 | 1 | — | |

TABLE 1-continued

Defoaming data for the "test" and "control" Cardiotomy reservoirs. All hold-up, wicking, and streaming height measurements were made relative to the constant 500 mL reservoir level. Activated clotting times were maintained at 4 × BL.

| Device | Elapsed Time (mins) | Test Period | Qg (LPM) | Qb (LPM) | Inlet Pressure (mmHg) | Hold-Up Height (in.) | Wicking Height (in.) | Streaming Height (in.) | Observations |
|---|---|---|---|---|---|---|---|---|---|
| Study #2 | 33 | 2 | 1 | 1 | 0 | NC | NC | — | |
| | 70 | 3 | 2 | 2 | 17–22 | NC | 6 | 6 | Wicking up the seam. |
| | 103 | 4 | 3 | 3 | 56 | NC | Maximum | — | 2 inches of foam. FAILURE |
| Control Study #2 | 3 | 1 | 0.5 | 0.5 | 0 | 0.25 | 1 | — | |
| | 33 | 2 | 1 | 1 | 0 | NC | NC | — | |
| | 70 | 3 | 2 | 2 | 17–20 | NC | 2 | — | Spotting |
| | <103 | 4 | NS | NS | 65 | 6 | Maximum | Maximum | Spotting. 2.5 inches of foam. FAILURE |
| Test Study #3 | 2 | 1 | 0.5 | 0.5 | 1 | <0.5 | 1 | — | |
| | 32 | 2 | 1 | 1 | 2 | NC | NC | — | Wicking up the seam. |
| | 68 | 3 | 2 | 2 | 23–30 | 0.5 | NC | — | Spotting. |
| | 101 | 4 | 3 | 3 | 50–57 | 2 | NC | — | Slight scud. |
| Control Study #3 | 2 | 1 | 0.5 | 0.5 | 0 | <0.5 | 1 | — | |
| | 32 | 2 | 1 | 1 | 0 | NC | NC | — | |
| | 68 | 3 | 2 | 2 | 12–45 | 0.5 | 2 | — | Spotting. |
| | 101 | 4 | NS | NS | 57–60 | 1 | 1.5 | 1.5 | Streaming. Increasing foam. FAILURE |

(NC = no change in a study parameter; NS = no sample measured; "—" parameter was non-existent at measurement.)

EXAMPLE 2

A Polyurethane defoamer was dip-coated in five percent (5%) weight per volume of Antifoam A® (polydimethylsiloxane and silicon dioxide). 10.0 ml of 0.1% stearylkonium heparin was spray coated onto the "test" defoamer, which was subsequently assembled into a cardiotomy reservoir. A "control" cardiotomy reservoir was used which had been coated with Antifoam A® only.

Two test studies were performed according to the following regimen: Anticoagulated bovine blood was introduced into the "control" and "test" cardiotomy reservoirs at the flow rate of three liters per minute. Air was also introduced into the cardiotomy reservoirs at a flow rate of three liters per minute, where it was mixed with the blood. The "foamed" blood was then constantly recirculated through the cardiotomy reservoirs at a rate of three liters per minute where air was constantly introduced at the same flow rate.

In the first test study, both cardiotomy reservoirs were examined after thirty, sixty and one hundred five minutes, at which times they continued to perform. After one hundred seventy minutes, the "control" unit accumulated one-half inch of foam, whereas the "test" unit showed small bubbles, but no accumulation of foam.

In the second test study, the units were examined after thirty, fifty-six and one hundred two minutes, and no bubbles were evident. After one hundred twenty-four minutes, both units exhibited trace bubbles. After one hundred seventy-two minutes, the "control" unit exhibited large bubbles whereas the "test" unit exhibited only small bubbles.

Thus, the defoaming efficiency of the cardiotomy reservoir with both heparin and Antifoam A® was equal to or better than the defoaming efficiency of the cardiotomy reservoir treated only with Antifoam A®.

EXAMPLE 3

0.5 gram of stearylkonium heparin and 20 grams of Antifoam A® (polydimethylsiloxane and silicon dioxide) were dissolved in a mixture of Freon TF and alcohol. Two urethane defoamers were dip-coated in the solution, dried, and assembled into hard shell venous reservoirs for two integrated membrane oxygenators. The thrombogenicity was evaluated by performing ex-vivo bifurcated extracorporeal test studies with a single bovine. The two oxygenators were connected in parallel to the bovine, one containing the "control" defoamer treated only with Antifoam A® and the other containing the "test" defoamer treated with the composite coating of heparin and Antifoam A®. Venous blood from the animal was bifurcated into the reservoirs and subsequently pumped into the membrane oxygenators. The oxygenated blood was then recombined and returned to the animal. The bifurcated circuit design permitted a direct comparison of the "test" and "control" units without animal-to-animal variations.

After six hours, the "control" defoamer exhibited extensive red thrombi, whereas the "test" defoamer showed little or no evidence of thrombus formation. Thus, the non-thrombogenic nature of the composite coating was demonstrated.

EXAMPLE 4

2.0 grams of benzalkonium heparin and 50 grams of Antifoam A® (polydimethylsiloxane and silicon dioxide) were dissolved in a mixture of Freon TF and alcohol. A "test" unit of Polyethylene mesh was dip-coated in the solution and subsequently air dried. A "control" mesh was treated with just Antifoam A®. Defoaming efficiency was determined by recirculating prefoamed blood through the "test" and the "control" mesh. The prefoamed blood was created by purging air into anticoagulated blood. The time required for the blood bubbles to breakthrough the "test" mesh was 23 minutes whereas the time for the blood bubbles to "break through" the "control" mesh was 25.7 minutes. Thus, the defoaming efficiency of the "test" unit was at least as good, if not better than, the defoaming efficiency of the "control" unit. The results suggested that the use of heparin with Antifoam A® did not alter the defoaming efficiency.

As borne out by the above examples and test results, it is possible, with the present invention, to create a surface for a medical device that exhibits both blood compatibility and effective defoaming capability. The embodiments described herein are merely exemplary and changes and modifications in the specifically described embodiments can be carried out by one skilled in the art without departing from the scope of the invention. All such changes and modifications are intended to be included within the scope of the invention as defined in the appended claims.

What is claimed is:

1. An antithrombogenic defoaming medical device comprising a medical device having a surface which contacts blood mixed with air, said surface having applied thereto sequential coatings of a solution of an antithrombogenic heparin species and a defoaming liquid mixture of a polysiloxane and silicon dioxide.

2. The medical device of claim 1 wherein said medical device is an extracorporeal blood processing device.

3. The medical device of claim 1 wherein said heparin species is a quaternary ammonium complex of heparin.

4. The medical device of claim 1 wherein said polysiloxane is a polydimethyl siloxane.

5. The medical device of claim 1 wherein said heparin species is a member selected from the group consisting of acetyl ammonium heparin, stearyldimethylbenzyl ammonium heparin, benzalkonium heparin, and tridodecylmethyl ammonium heparin.

6. The medical device of claim 5 wherein said medical device is an extracorporeal blood processing device.

7. A method for providing an antithrombogenic defoaming blood contacting surface which comprises applying to a surface, which contacts blood mixed with air, sequential coatings of a solution of an antithrombogenic heparin species and a defoaming liquid mixture of a polysiloxane and silicon dioxide.

8. The method of claim 7 wherein said surface is a surface of an extracorporeal blood processing device.

9. The method of claim 7 wherein said heparin species is a quaternary ammonium complex of heparin.

10. The method of claim 7 wherein said heparin species is a member selected from the group consisting of acetyl ammonium heparin, stearyldimethylbenzyl ammonium heparin, benzalkonium heparin, and tridodecylmethyl ammonium heparin.

11. The method of claim 7 wherein said polysiloxane is a polydimethyl siloxane.

12. The method of claim 7 wherein said blood contacting surface is a surface of a medical device.

13. A method for providing an antithrombogenic defoaming medical device which comprises the steps of:

(a) applying to a surface of a medical device, which contacts blood mixed with air, a liquid mixture of a polysiloxane and silicon dioxide, and (b) applying a solution of a quaternary ammonium complex of heparin to the surface to which said liquid mixture has been applied.

14. An antithrombogenic defoaming medical device prepared according to the method of claim 7.

15. An antithrombogenic defoaming medical device prepared according to the method of claim 13.

* * * * *